United States Patent [19]

Roux

[11] 3,978,336
[45] Aug. 31, 1976

[54] HYBRID SCINTILLATION SCANNING APPARATUS

[75] Inventor: Georges Roux, Paris, France

[73] Assignee: Compagnie Generale de Radiologie, Paris, France

[22] Filed: Jan. 6, 1975

[21] Appl. No.: 538,800

[30] Foreign Application Priority Data
Jan. 10, 1974  France .............................. 74.00812

[52] U.S. Cl. ................................. 250/366; 250/369
[51] Int. Cl.² ............................................ G01T 1/20
[58] Field of Search ................ 250/363 S, 366, 369

[56] References Cited
UNITED STATES PATENTS

| | | | |
|---|---|---|---|
| 3,432,660 | 3/1969 | Anger | 250/363 S |
| 3,509,341 | 4/1970 | Hindel et al. | 250/363 S |
| 3,688,113 | 8/1972 | Miraldi | 250/370 X |
| 3,717,763 | 2/1973 | Tanaka | 250/363 S |
| 3,857,036 | 12/1974 | Novak | 250/367 |

*Primary Examiner*—Harold A. Dixon
*Attorney, Agent, or Firm*—Edwin E. Greigg

[57] ABSTRACT

The invention relates to a hybrid scintillation scanning apparatus. Said apparatus comprises: a scintillation crystal bar of elongated form receiving the gamma radiation through a collimator and comprising a transparent upper face optically coupled by means of a light guide to a plurality of photomultipliers. The photomultipliers furnish their signals to an electronic combining circuit supplying, on one hand, an amplitude analyzer and, on the other hand, a computing circuit permitting the location of the scintillation along the axis of the bar.

6 Claims, 7 Drawing Figures

HYBRID SCINTILLATION SCANNING APPARATUS

The present invention relates to hybrid scintillation apparatus or apparatus for scintillation exploration by scanning which permits in particular forming scintigrams of distribution of a radio-isotope introduced within a part, or the whole, of the human body by scanning in a longitudinal direction of the body.

Known devices of this type, for example those described in an article by DAVIS and MARTONE "The Hybrid Radio-isotope Scanner" pages 114 to 127, of the *American Journal of Nuclear Medicine*, Vol. 7, 1966 and in the U.S. Pat. No. 3,688,113 filed June 22, 1970, comprise essentially a collimator which delimits the considered radiation zone in the region of the source, a crystal placed behind this collimator, the length of which crystal is distinctly greater than the width, whereas its cross-section may be circular or rectangular. The radiations passing through the collimator are converted into light by the scintillator in the form of scintillations which are well located within the volume of the scintillator. The position of the scintillation in the direction of the length of the crystal is determined by means of two photomultipliers, each placed at each end of the crystal, and converting the light received by their photocathode into an electrical pulse.

Owing to the fact that this crystal is considered, in the direction of its length, to be a light guide and possesses an approximately exponential attenuation of the light, the sum and the difference of the logarithms of the amplitudes of the pulses received at the anodes of the photomultipliers are linearly related, in respect of the sum, to the amplitude of the scintillation and, in respect of the difference, to the position of the scintillation. These magnitudes, namely amplitude and position of the scintillation, are fundamental, since the amplitude permits measuring the energy of the incident radiation and, consequently, eliminating parasitic radiations, and the position permits determining the distribution of the radioactive substance in the object examined.

The precision of the determination of these magnitudes is therefore a fundamental characteristic of this type of device. This precision depends directly on the number N of photoelectrons emitted by the photocathodes of the photomultipliers, by a relation involving the inverse of the square root of this number N. As the principle of the method described in the aforementioned documents essentially implies an exponential process of attenuation of the light, the number of photons reaching the photocathodes is considerably reduced with respect to number in fact emitted in the course of the scintillation. Moreover, the coefficient of exponential attenuation appears in the formulae giving the variance on the energy and position measurements, as a function of the scintillation position. This leads to a variation in the spatial resolution — precision of the location — and in the energy resolution — precision of the measurement of energy — as a function of the position of the scintillation. In such a method the length of the crystal is limited by this practically exponential attenuation of the light to a dimension generally less than the width of a human body.

Another known apparatus of this type, described in French Pat. No. 1,524,742 of May 29, 1967, and corresponding to U.S. Pat. No. 3,509,341, comprises an exploring device which comprises essentially a linear assembly consisting of a plurality of juxtaposed channels each one of which comprises a collimator, a scintillation crystal, a light guide and a photomultiplier. The crystals are separated from each other by reflecting surfaces so that the light generated in each one thereof only feeds the photocathode of the associated photomultiplier. Each one of the collimators is focused on a single exterior point so that the assembly furnishes the scintigraphic image of a plurality of distinct focal points which are disposed on a straight line parallel to the axis of the assembly at distances equal to the width of the crystals. Such a device does not permit the exploration of a part, or the whole, of the body by a single scan in a direction perpendicular to the straight line connecting the focal points, but requires also movements parallel to this straight line.

The device according to the present invention avoids the drawbacks of the various devices mentioned hereinbefore. In the device according to the invention, the spatial resolution and the energy resolution are very much improved and constant throughout the effective length of the crystal and consequently it permits obtaining a scintigram of the whole body by means of a single scan in a direction parallel to the body, since the length of the crystal, or of an end-to-end juxtaposition of a plurality of crystals is not limited.

There is provided according to the invention a hybrid scintillation scanning apparatus for locating radiations emanating from an object and comprising: a scintillator bar of elongated shape converting incident radiations into luminous scintillations; a collimator disposed in proximity to the bar so as to transmit radiations to the bar by defining in the region of the object a linear radiation field parallel to the axis of the bar; and a plurality of photomultipliers whose photocathodes are coupled to the bar by light guides; wherein said scintillator bar comprises a transparent planar lateral face extending throughout its length and differing from the face near to the collimator, the other lateral faces of the bar being frosted and covered with a material diffusing light, said transparent face is connected by means of an optical joint to said light guide of elongated shape whose face opposed to that connected to the transparent face is connected by means of optical joints to the photocathodes of said photomultipliers, and said photomultipliers are disposed in equally spaced relation along the light guide in front of said transparent face of the bar so as to detect the scintillations produced by the bar; said apparatus further comprising a conventional electronic computer circuit locating the scintillations along the bar as a function of the signals furnished by all of said photomultipliers.

The invention will be better understood and other features and advantages thereof will be apparent from the ensuing description with reference to the accompanying drawings given by way of example and in which.

Figure 1:
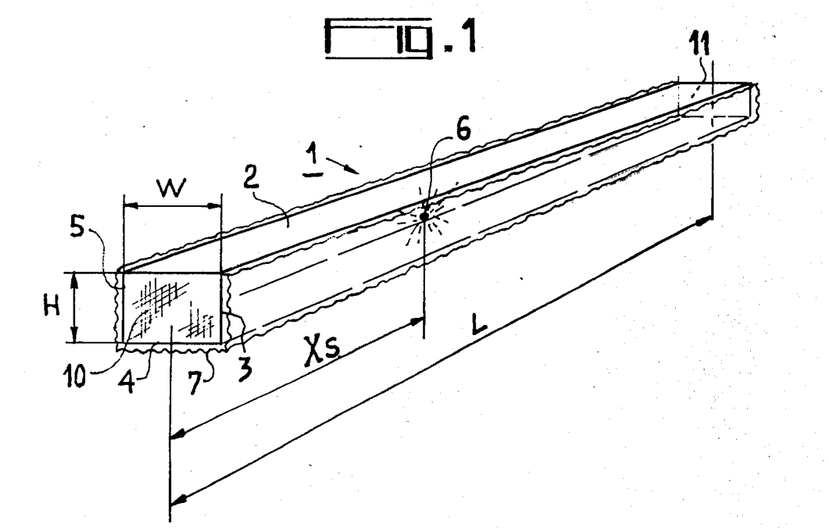
FIG. 1 is a perspective view of a scintillating bar of elongated shape of utility in an apparatus according to the invention.

FIG. 1 illustrates in perspective a scintillating bar 1 formed by a crystal of sodium iodide (NaI) activated with thallium (Tl) of homogeneous structure. The crystal 1 has a length L distinctly greater than its width W and its height H and has a rectangular cross-section in the illustrated embodiment. Note that the cross-section may also be trapezoidal or semicircular; in the first case, the widest face and, in the second, the planar face are disposed facing the photomultiplying tubes adapted to convert the luminous scintillations generated by the gamma rays into electrical pulses and to determine by means of a computer circuit the position of each scintillation.

The scintillator crystal 1 comprises a planar face 2 which is transparent to light and is generally in optical contact with a transparent protecting plate of a light-conducting material, and three other faces 3, 4 and 5 which are frosted and covered with a layer 7 of a light-diffusing material (white colour) such as magnesium oxide (MgO) or aluminium oxide ($Al_2O_3$).

Figure 2:
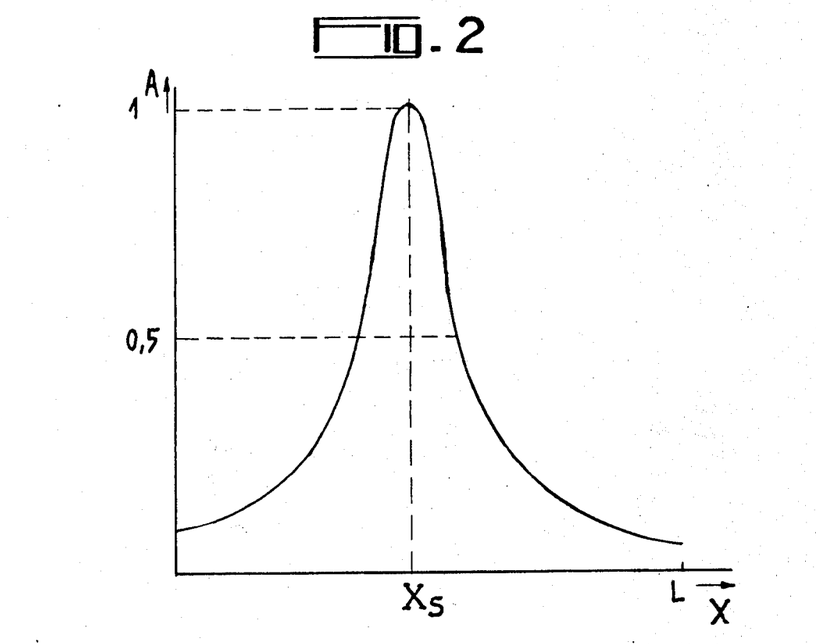
FIG. 2 is a diagram representing the relative quantity of light measured on the transparent lateral face 2 of the bar 1 shown in FIG. 1, as a function of the coordinate X parallel to the axis of the bar, by displacing a photomultiplier along said face when a scintillation is produced at a distance $X_s$ from one of the ends of the bar 1.

FIG. 2 illustrates the distribution (curve A) of the light emerging from the transparent face 2 of the crystal 1 and measured by a photomultiplier (not shown) having a circular photocathode whose diameter is in the neighbourhood of the width W of the crystal 1, when a scintillation 6 is produced by means of a point source of gamma rays and a collimator (not shown) at a distance $X_s$ from one end ($X = O$) of the bar 1. This distribution, in which the value A indicates the relative quantity of light with respect to its maximum value, is a narrow bell-shaped centered on the coordinate $X_s$ of the scintillation. To effect this measurement, the photomultiplier has been displaced along the bar 1 in a direction parallel to the axis of the latter. When a light guide is interposed between the bar 1 and the photocathode of the measuring photomultiplier so as to shift it away from the transparent face 2, the width of the curve A (bell) increases as a function of the distance between the face 2 and the photocathode, since the quantity of light measured by the photocathode is proportional to the solid angle of a cone the apex of which is located at the region 6 of the scintillation and the base of which is defined by the periphery of the photocathode. This widening of the distribution curve may be employed for ensuring a more linear restitution of the coordinate X by the combination of the electrical signals furnished by a plurality of photomultipliers (see FIG. 3) optically coupled to the transparent face 2.

Figure 3:
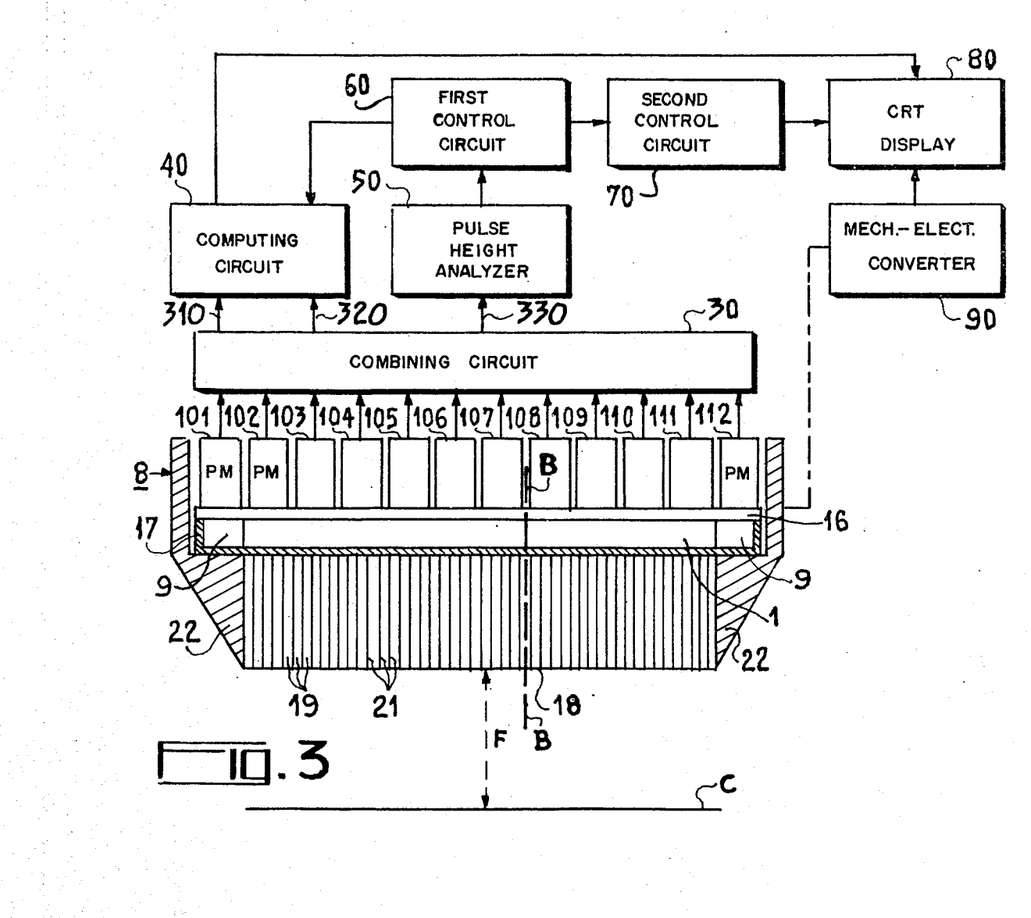
FIG. 3 is a longitudinal sectional view of the assembly of the scanning head and, in the form of a simplified block diagram, the circuit processing the scintigrams.

FIG. 3 shows in longitudinal section the assembly of the scanning head of a hybrid scintillation apparatus comprising a scintillator bar described hereinbefore and shown in FIG. 1 and, in the form of a simplified block diagram, a circuit for processing the scintigrams.

Figure 4:
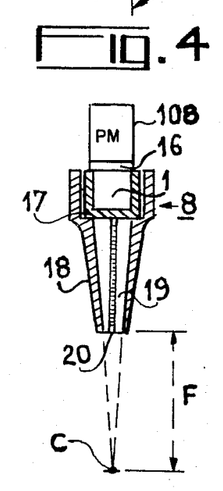
FIG. 4 is a cross-sectional view taken on line B-B of the scanning head.

FIG. 4 is a cross-sectional view, taken on line B—B of the scanning head shown in FIG. 3.

Figure 5:
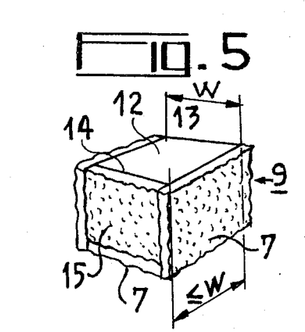
FIG. 5 is a perspective view of a light conducting part 9 shown in FIG. 3.

This scanning head 8 according to the invention comprises a scintillator bar 1 shown in FIG. 1 having a length L which may be for example as much as 60 cm which is usually sufficient for effecting a scintigraphy of whole body. The two faces 10, 11 (FIG. 1) of the crystal 1 are perpendicular to its longitudinal axis, located respectively at its opposite ends, and transparent (polished) and connected by means of optical joints to end members 9 of a light-conducting material having an index of refraction very near to that of the scintillating bar. These members 9, illustrated in FIG. 5, have a cross-section which is substantially identical to that of the crystal 1 and a length less than, or equal to, the diameter of the photocathode of the photomultiplying tubes employed in the circuit and they are preferably constructed by using unactivated sodium iodide (NaI) crystals when the bar 1 is of sodium iodide activated with thallium. The lateral faces of these light-conducting members 9 located respectively in the extension of the faces 3, 4 and 5 of the crystal 1, are also frosted and covered with the same diffusion layer 7 (of white colour) as that which covers the faces 3, 4 and 5. The upper lateral face 12 of the member 9 located in the extension of the transparent face 2 of the crystal, is also preferably transparent. The interior transverse face 13 of the members 9 adapted to be connected to one of the transverse faces 10 or 11 (FIG. 1) of the crystal by means of a conventional optical joint (employing for example special transparent adhesive, Canada balsam or silicone oil) is also perfectly transparent (polished) whereas the exterior transverse face 14 constituting the opposite ends of an assembly comprising a scintillating bar 1 and two conductive members 9, is frosted and covered with a layer 15 of a light-absorbing material (black colour such as a varnish called "aquadag"). The extension of the scintillating bar 1 by members 9 which are non-scintillating but conductive of light and moreover do not receive gamma radiation, permits obtaining, on one hand, an improvement in the linearity of response of the assembly of the scanning head and, on the other hand, uniformity of response at the edges of the detection field. The assembly comprising the crystal 1 and the two conductive members 9 is contained in a closed moisture-tight casing (NaI being hygroscopic) whose part adjacent the transparent faces 2 and 12 of the crystal 1 and the members 9 is a rectangular plate 16 of a light-conducting material connected to these transparent faces by an optical joint, the remainder of the case 17 being metallic, opaque to visible light and transparent to X or gamma rays.

A longitudinal collimator 18 of a material opaque to gamma radiation (such as lead, tungstene or gold) and comprising numerous elongate openings 19 essentially perpendicular to the longitudinal axis of the bar 1 and, in FIGS. 3 and 4, also perpendicular to the lower lateral face 4 (FIG. 1) of the bar.

These openings 19, of rectangular section, are here formed by four exterior walls defining a space of elongated rectangular horizontal section whose width varies with the height of one or more longitudinal partition walls 20 and numerous transverse partition walls 21 perpendicular to the walls 20. The length of this downwardly tapering space having the openings 19, extends over a length L equal to that of the crystal 1 whose lower face 4 faces the upper ends of these openings, the light-conducting members 9 facing opaque edges 22 of the collimator 18.

The cross-section of the space defined by the lateral walls of the collimator 18 being trapezoidal with the large base in the vicinity of the face 4 of the crystal 1, the collimator defines a linear field C in the region of the radioactive object focused on a straight line parallel to the longitudinal axis of the scintillator bar and located at a distance F from the lower edge of the collimator 18.

A predetermined number depending on the length of the scintillating bar 1, for example 12 photomultipliers 101 to 112 for a bar 1 having a length of 60 cm, are coupled to the transparent face 2 of the bar and to the faces 12 of the members 9 through the light-conducting plate 16, preferably by means of an optical joint between the photocathode and the upper face of this plate 16; the portions of the plate 16 which are not in contact with the photomultipliers, the crystal 1 and the members 9, are rendered opaque to light, as are the glass envelopes of the photomultipliers. The photomultipliers 101 and 112, respectively located at the two ends of the scanning head 8, have photocathodes located, at least in part, in facing relation to the upper transparent faces (12, FIG. 5) of the light-conducting end members 9.

Each one of the photomultipliers 101 to 112 has an output furnishing in response to a scintillation produced in the bar 1 a signal whose amplitude is proportional to the intensity of the light received by the respective photocathode. These outputs feed a first circuit 30 termed a combining circuit having preamplifiers and devices for combining the signals from the photomultipliers either by means of a network of resistors, summing and subtracting circuits one embodiment of which has been in FIG. 6, or by means of delay lines time measuring and shaping electronic circuits, one embodiment of which has been shown in FIG. 7.

The first circuit 30 has two first outputs 310 and 320 feeding a computing circuit 40 which supplies in the form of electrical signals the coordinate X of the scintillation and consequently of the source of radiation irradiating the scintillator bar 1, and a second output 330 connected to a pulse height or amplitude analyzer or discriminator 50 which selects the scintillations corresponding to the direct incident radiation and eliminates the spurious scintillations and those due to the diffused radiations which have a luminosity which is lower than on usually different from the first. The amplitudes of the pulses corresponding to the scintillations due to the direct radiation are within a predetermined range, the analyzer 50 having settings permitting a choice of this range in accordance with the nature of the radio-isotope which constitutes the source of radiation to be located.

The amplitude analyzer 50 furnishes pulse signals to a first control circuit 60 permitting validating the calculation of the coordinate X when the amplitude of the pulse which it receives is within this aforementioned range. The control circuit 60 feeds, on one hand, the computing circuit 40 and, on the other, a second control circuit 70 furnishing control signals to a device 80 displaying or recording the coordinates of the scintillations measured by the scanning head 8 which is displaced at constant speed in a direction perpendicular to the longitudinal axis of the crystal 1. In addition to these control signals, the device 80 receives signals corresponding to the coordinate X furnished by the computing circuit 40 and signals corresponding to the coordinate Y which indicates the position of the scanning head 8 and is furnished by a mechanical-electrical converter 90 coupled to the mechanism (not shown) driving the head which may be constructed in the conventional manner.

Figure 6:
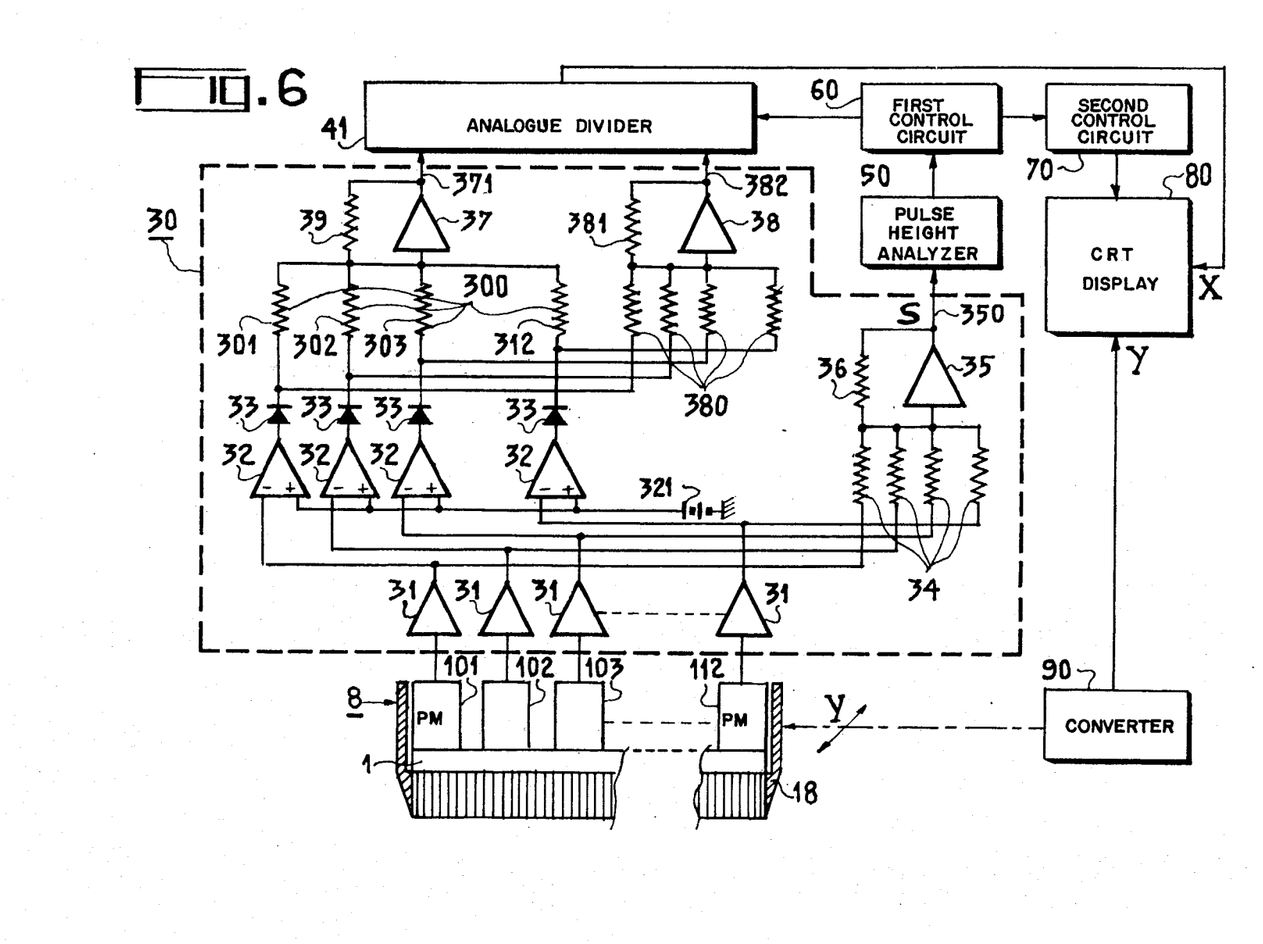
FIG. 6 is a block diagram of a hybrid scintillation apparatus according to the invention employing a first embodiment of an electronic coordinate computing circuit.

FIG. 6 illustrates an embodiment of the summation circuit 30 comprising a network of resistors for combining the signals furnished by the different photomultipliers 101 to 112. A circuit employing an analogue principle for the determination of the coordinates X and Y has been described in U.S. Pat. No. 3,011,057 filed Jan. 2, 1958 and concerning a scintillation camera.

Among the advantages of a network of resistors there may be noted the ease and consequently the low cost, of the construction and the great rapidity of the processing of the coordinates ensuring such a system minimum loss of time.

The combining circuit 30 shown in FIG. 3 comprises essentially 12 conventional low-noise preamplifiers 31 respectively fed by the outputs (anode) of the photomultipliers 101 to 112. The output of each one of the preamplifiers 31 feeds, on one hand, a threshold amplifier 32, 33 comprising for example a differential amplifier 32 and a diode 33 arranged in cascade and, on the other hand, a resistor 34 of value $R_{34}$ connected to the input of a first operational amplifier 35 having a feedback resistor 36 of value $R_{36}$ connected between its output and its input. The twelve resistors 34, which constitute a first adder or summing network respectively connecting the outputs of all the amplifiers 31 to the single input of the operational amplifier 35, form with the latter a first adder or summing circuit the output 350 of which furnishes a signal proportional to the sum of the signals S of the photomultipliers and consequently to the energy of the gamma radiation which produces the scintillations.

This signal S, which is proportional to energy of the radiation, is applied to the amplitude analyzer 50 mentioned hereinbefore for recording only the scintillations whose light intensity is within the range of energies corresponding to the radio-isotope employed.

The twelve signal inverting inputs (−) of the differential amplifiers 32 are respectively fed by the outputs of the twelve preamplifiers 31 whereas their non-inverting threshold inputs (+) are connected in parallel to the positive terminal of a source of voltage 321 furnishing a threshold voltage $E_s$. They therefore furnish at their outputs positive voltages when their signal input receives voltages exceeding in absolute value the threshold voltage $E_s$, or negative voltages, when their input signal is lower in absolute value to this voltage $E_s$. The diodes 33 connected downstream of the amplifiers 32 eliminate the negative voltages and only allow through signals whose amplitudes at the input are higher than $E_s$. Consequently the signals issuing from the photomultipliers remote from the place of scintillation and therefore weakly illuminated and consequently giving rise to fluctuations in the number of photoelectrons emitted, and spurious signals and noise due to diffusion of the light and of the gamma radiation in the crystal 1, multiplied by coefficients of location, which constitute sources of error in the calculation of the coordinate X, are in major part eliminated. The threshold amplifier therefore multiplies the input signal $S_2$ by a coefficient $K_i$ ($i = 1$ to 12) which has the value 0 or +1 according to the amplitude of $S_i$. It is moreover possible to apply different threshold voltages to each one of the amplifiers 32. The twelve diodes 33 whose cathodes constitute the respective outputs of the threshold amplifiers feed respectively a first resistive summation network 300 and a second resistive summation network 380. The first summation network comprises twelve resistors 301 to 312 of different values $R_{301}$ to $R_{312}$ which are chosen as a function of the position $X_i$ ($i = 1$ to 12) of the photomultipliers 101 to 112 which feed them through the elements 31, 32 and 33. The resistors 301 to 312 therefore each connect diodes 33 to the single input of a second operational amplifier 37 having a negative feed-back resistor 39 of value $R_{39}$. Each one of the signals $S_i$ furnished by the threshold amplifiers is therefore multiplied by a location or position coefficient $a_i = R_{39}/R_i$ ($i = 1$ to 12) which is linearly related to the position $X_i$ of the respective centers of the photocathodes of the photomultipliers 101 to 112, that is to say, $a_i = b - X_i$ in which $b$ is constant, the signals $S_i$ are therefore multiplied at the output by a coefficient which is proportional to the coordinate $X_i$ of the position of the photo multiplier furnishing it. The second operational amplifier therefore furnishes a signal $$N = \sum_{i=1}^{12} k_i a_i S_i = b \sum_{i=1}^{12} k_i X_i S_i$$

The second summation network 380 comprises twelve resistors of the same value $R_{380}$ which connect each one of the diodes 33 to the single input of a third operational amplifier 38 having a negative feed-back resistor of value $R_{381}$. The third operational amplifier 38 therefore furnishes at its output a signal $$D = c \sum_{i=1}^{12} k_i S_i ,$$

in which $c = R_{381}/R_{380}$ is a constant.

It can be shown that the ratio $Q = N/D$ of the signals $N$ and $D$ respectively furnished by the second, 37, and the third, 38, operational amplifier, that is to say, $$Q = d \; \frac{k_1 X_1 S_1 + ... + k_{12} X_{12} S_{12}}{k_1 S_1 + ... + k_{12}S_{12}}$$

in which $d = b/c$ which are constants, a practically linear relation of the coordinate X of the scintillation.

The outputs 371 and 382 respectively furnish the signals N and D and respectively feed them to suitable inputs of an analogue divider 41 effecting, by the division of the input signals, the computation of the ratio Q and, consequently, of the coordinate X of the scintillation.

Figure 7:
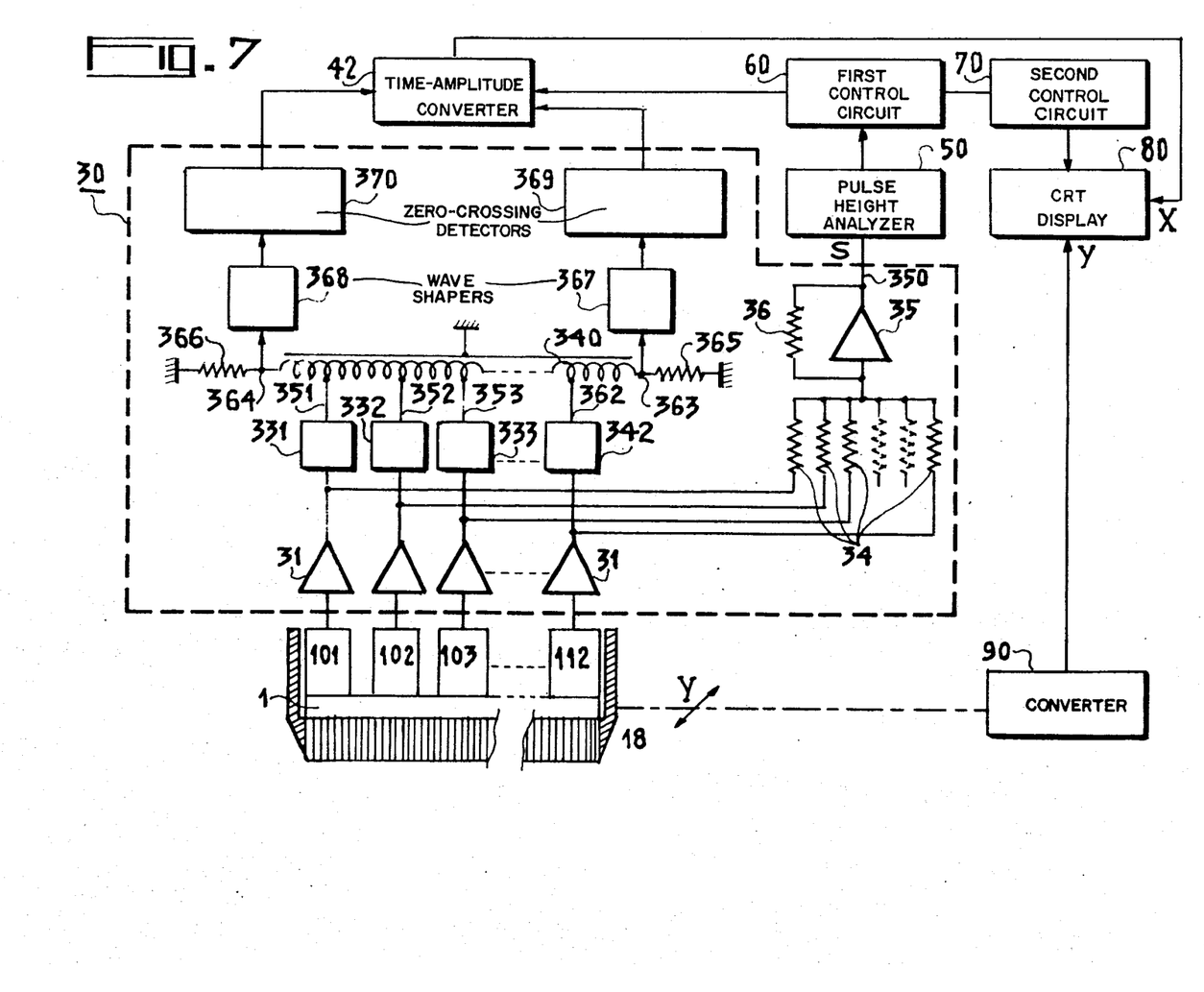
FIG. 7 is a block diagram of an apparatus of a second embodiment known per se of such a computing circuit.

FIG. 7 represents a combining circuit 30 and a computing circuit 42 employing a delay line for combining the signals from the photomultipliers, the principle of operation of which is described in U.S. Pat. No. 3,691,379 filed Oct. 1, 1970.

The utilization of delay lines permits excluding from the computation of the coordinates the photomultipliers remote from the scintillation and consequently eliminating the aforementioned effect of the multiplication of noise and spurious signals coming from the photomultipliers weakly illuminated by the coefficient of the position, but results in a time delay whose duration is determined by the time of propagation of the pulses in the delay line.

In the circuit shown in FIG. 7, the photomultipliers 101 to 112 also feed preamplifiers 31 the respective outputs of which feed, on one hand, a first summing or adder circuit 34, 35 and 36 similar to that shown in FIG. 6, and, on the other hand, current generators 331 to 342.

Each one of these current generators 331 to 342 has a high output impedance so as not to mismatch the delay line 340 which it feeds through one of the taps 351 to 362. These taps 351 to 362 of the delay line 340 are spaced apart in such manner that the interval of delay undergone by the signals passing therethrough is proportional to the respective coordinates $X_i$ of the centres of the photocathodes of the photomultipliers 101 to 112.

The terminals 363 and 364 located at the two ends of the delay line 340 constitute the respective outputs of the latter and they are respectively loaded by resistors 361 and 366 the value of which is equal to the characteristic impedance $Z_c$ of the line 340. It is the photomultipliers which are the nearest to the scintillation which produce signals of the largest amplitude the whole of which produces two pulses at the respective outputs 365 and 366 of the delay line 340, the instants $t_1$ and $t_2$ of appearance of the respective maxima being a function of the position of the scintillation in the crystal 1.

These outputs 365 and 366 respectively feed shaping circuits 367 and 368 which convert the monopolar signals into symmetrical bipolar signals with the aid of a network comprising delay lines (see U.S. Pat. No. 3,691,379) or a differentiator circuit to obtain, in each one of the signals, a zero-crossing time corresponding to the instants $t_1$ and $t_2$ of the appearance of the amplitude maxima of the output signals of the delay line 340, so as to determine these instants with precision.

The shaping circuits 367 and 368 respectively feed zero-crossing detectors 369 and 370 furnishing pulses at the zero-crossing times of their input signals, that is to say, at instants $t_1$ and $t_2$.

The zero-crossing detectors 369 and 370 supply a circuit computing the time difference 42 between the instants $t_1$ and $t_2$, this difference $t_2 - t_1$ being proportional to the coordinate X of the scintillation. The computing circuit 42 receives moreover from the amplitude analyzer 50 (through the control circuit 60) a pulse at instant $t_0$, this pulse resulting from the summation of the signals of all the photomultipliers 101 to 112; the time $t_0$ corresponding to the instant of the production of the scintillation in the crystal 1.

For calculating the time difference, the computing circuit 42 has time-amplitude converters comprising, for example, a saw-tooth generator and furnishing signals whose amplitude is proportional to the lapse of time between the signal at instant $t_0$ triggering the start of the linear saw-tooth and the appearance of a pulse furnished at instant $t_1$ and/or $t_2$ by one of the zero-crossing detectors 369 or 370, and a differential amplifier furnishing a signal proportional to the difference of the respective amplitudes of the saw-tooth at instants $t_1$ and $t_2$.

It will be observed here that, in order to determine the coordinate of the scintillation, it is sufficient to employ only one of the outputs of the delay line 340, a single wave forming circuit and to detect the zero-crossings, the computing circuit 42 solely effecting the time-amplitude conversion for $t_1 - t_0$.

It will also be observed that the device displaying and recording the coordinates 80 is constructed in the conventional manner and can therefore comprise an oscilloscope the deflection plates of which respectively receive the coordinate X of the computing circuit 40 (FIG. 3) – 41 (FIG. 6) or 42 (FIG. 7), the coordinate Y of the mechanical-electrical converter 90 coupled to the scanning mechanism and the control signal of the beam controlled by the amplitude analyzer 50 which can unblank the beam of electrons of the cathode ray tube of the oscilloscope. The device 80 can also include a mass memory electronic computer permitting the storage of the coordinate of a scintillation in a numerical form.

The apparatus just described and illustrated in FIGS. 3, 6 and 7 is a hybrid scintillation scanner which may be employed for furnishing an image of the distribution of a radio-isotope marking a biological molecule, an example of which is the detection of lesions or metastasis of the bone.

The construction of such an apparatus is simple since a single mechanical movement is required: the detecting head is fixed to a carriage movable on a rail parallel to the bed of the patient. The device described may be employed for any application in which the distribution of a radioactive substance must be determined with precision over large areas.

What is claimed is:

1. A hybrid scintillation scanning apparatus for locating radiation emanating from an object and comprising: an elongated scintillation crystal bar for converting the incident radiations into luminous scintillations provided with at least one planar and transparent face, adapted to transmit the light of the scintillations to the exterior of the bar; a collimator located in proximity to and facing one of the lateral faces of the bar for transmitting radiations to the whole of the bar and defining in the region of the object a linear radiation field parallel to the axis of the bar; and a plurality of photomultipliers whose photocathodes are optically coupled to the transparent faces of the bar by means of optical joints and/or light guides; and an electronic computing circuit for locating the scintillations along the bar as a function of the signals delivered by all of said photomultipliers; wherein said transparent face of the scintillator bar optically coupled to said photomultipliers is constituted by one of its lateral faces extending throughout its length and distinct from the one facing the collimator, said transparent lateral face being of rectangular shape and having a width substantially equal to the diameters of said photocathodes to which it is connected by means of a light guide of elongated shape comprising a first face optically coupled to said transparent face by covering it completely and a second face, opposite said first face, optically coupled to the photocathodes of said photomultipliers, said photomultipliers being disposed at equal distances apart along said second face of the light guides and in facing relation to said transparent face of the bar so as to detect scintillations produced by the bar; all the other lateral faces of the scintillator bar distinct from the transparent lateral face being frosted and covered with a layer of a light-diffusing material so as to prevent reflections therefrom.

2. A scintillation apparatus as claimed in claim 1, of the type in which the transverse faces located at the end of the bar are transparent, the apparatus further comprising two light-conducting end members of a material having an index of refraction close to that of the bar and disposed in the extension of the bar; said members having a cross-section identical to that of the bar and a length less than, or equal to, the width of the bar and each comprising: a first transparent transverse face coupled by means of an optical joint to one of the transparent transverse faces of the bar, a second transverse face opposed to the first transverse face and frosted and covered with a light-absorbing material, a transparent lateral face disposed in alignment with the transparent lateral face of the bar and coupled by an optical joint to one of the extensions of said light guide, the other lateral faces of said members being frosted and covered with a diffusing material, said extensions of the light guide being respectively optically connected by their faces opposite the transparent faces of said members to at least one part of the photocathodes of the two photomultipliers respectively disposed, at least in part, facing relation to said light-conducting members; said collimator directing the incident radiation only onto the bar, said end members located in the extension of the bar permitting the elimination of the non-linearity of the location in the vicinity of the two ends of the bar.

3. A scintillation apparatus as claimed in claim 1, wherein the electronic computing circuit comprises preamplifiers respectively supplied by said photomultipliers, a first adder circuit adding, by means of a network of resistors of the same value, the signals from all the preamplifiers, said first adder circuit feeding a pulse amplitude analyzer selecting signals whose amplitude is within a predetermined range corresponding to the energy of the incident radiation converted into light energy by said scintillator bar, threshold amplifiers respectively fed by said preamplifiers and transmitting the signals from the photomultipliers solely when their amplitude exceeds a predetermined threshold value, said threshold amplifiers respectively feeding a second adder-multiplier circuit comprising an operational amplifier whose input is connected to the respective outputs of the threshold amplifiers through resistors of different values chosen in accordance with the position of the photomultipliers along the bar so as to respectively multiply the signals from the photomultipliers by coefficients which are proportional to the coordinate of the location of the centres of their respective photocathodes; said threshold amplifiers supplying moreover a third adder circuit comprising an operational amplifier whose input is connected to the respective outputs of the threshold amplifiers through resistors of the same value, said computing circuit further comprising an analogue divider effecting the division between the amplitudes of the signals respectively from the second and the third adder circuits, the ratio between these two amplitudes being proportional to the coordinate of the scintillation produced by a radiation.

4. A scintillation apparatus as claimed in claim 2, wherein the electronic computing circuit comprises preamplifiers respectively supplied by said photomultipliers, a first adder circuit adding, by means of a network of resistors of the same value, the signals from all the preamplifiers, said first adder circut feeding a pulse amplitude analyzer selecting signals whose amplitude is within a predetermined range corresponding to the energy of the incident radiation converted into light energy by said scintillator bar, threshold amplifiers respectively supplied by said preamplifiers and transmitting the signals from the photomultipliers solely when their amplitude exceeds a predetermined threshold value, said threshold amplifiers respectively feeding a second adder-multiplier circuit comprising an operational amplifier whose input is connected to the respective outputs of the threshold amplifiers through resistors of different values chosen in accordance with the position of the photomultipliers along the bar so as to respectively multiply the signals from the photomultipliers by coefficients which are proportional to the coordinate of the location of the centres of their respective photocathodes; said threshold amplifiers supplying moreover a third adder circuit comprising an operational amplifier whose input is connected to the respective outputs of the threshold amplifiers through resistors of the same value, said computing circuit further comprising an analogue divider effecting the division between the amplitudes of the signals respectively from the second and the third adder circuits, the ratio between these two amplitudes being proportional to the coordinate of the scintillation produced by a radiation.

5. A scintillation apparatus as claimed in claim 1, wherein the electronic computing circuit comprises preamplifiers respectively supplied by said photomultipliers; an adder circuit adding the signals from all the preamplifiers, said adder circuit feeding a pulse amplitude analyzer delivering a signal at the instant of the production of a scintillation in the bar when the energy of the scintillation corresponds to the incident radiation to be detected; a delay line matched at its two ends and comprising taps respectively fed by said preamplifiers through current generators having a high output impedance and uniformly disposed along the line in such manner that the delays that the different signals injected through said taps undergo are respectively proportional to the coordinates of location of the centers of the photocathodes of the photomultipliers furnishing them, the outputs of the delay line furnishing signals which have their respective maxima at instants, the time intervals between these instants and the instant of production of the scintillation being respectively proportional to the distances between the position of the scintillation and the ends of the bar.

6. A scintillation apparatus as claimed in claim 2, wherein the electronic computing circuit comprises preamplifiers respectively supplied by said photomultipliers; an adder circuit adding the signals from all the preamplifiers, said adder circuit feeding a pulse amplitude analyzer delivering a signal at the instant of the production of a scintillation in the bar when the energy of the scintillation corresponds to the incident radiation to be detected; a delay line matched at its two ends and comprising taps respectively fed by said preamplifiers through current generators having a high output impedance and uniformly disposed along the line in such manner that the delays that the different signals injected through said taps undergo are respectively proportional to the coordinates of location of the centres of the photocathodes of the photomultipliers furnishing them, the outputs of the delay line furnishing signals which have their respective maxima at instants, the time intervals between these instants and the instant of production of the scintillation being respectively proportional to the distances between the position of the scintillation and the ends of the bar.

* * * * *